US008682447B2

(12) United States Patent
Bradley et al.

(10) Patent No.: US 8,682,447 B2
(45) Date of Patent: *Mar. 25, 2014

(54) APPARATUS AND METHOD FOR DETERMINING THE RELATIVE POSITION AND ORIENTATION OF NEUROSTIMULATION LEADS

(75) Inventors: Kerry Bradley, Glendale, CA (US); James R. Thacker, Eureka, MO (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1966 days.

This patent is subject to a terminal disclaimer.

(21) Appl. No.: 11/343,007

(22) Filed: Jan. 30, 2006

(65) Prior Publication Data
US 2006/0122654 A1 Jun. 8, 2006

Related U.S. Application Data

(63) Continuation of application No. 10/310,202, filed on Dec. 3, 2002, now Pat. No. 6,993,384.

(60) Provisional application No. 60/338,331, filed on Dec. 4, 2001.

(51) Int. Cl.
*A61N 1/00* (2006.01)

(52) U.S. Cl.
USPC .................................. 607/62; 607/2

(58) Field of Classification Search
USPC ............... 607/59–62, 27, 28, 117, 43, 2
See application file for complete search history.

(56) References Cited

U.S. PATENT DOCUMENTS

| | | | |
|---|---|---|---|
| 3,646,940 | A | 3/1972 | Timm et al. |
| 3,724,467 | A | 4/1973 | Avery et al. |
| 3,822,708 | A | 7/1974 | Zilber |
| 4,486,835 | A | 12/1984 | Bai et al. |

(Continued)

FOREIGN PATENT DOCUMENTS

WO WO-02/09808 A1 2/2002

OTHER PUBLICATIONS

Office Action dated Apr. 12, 2005 for U.S. Appl. No. 10/310,202, filed Dec. 3, 2002, inventor: Kerry Bradley, (6 pages).

(Continued)

*Primary Examiner* — Scott Getzow
(74) *Attorney, Agent, or Firm* — Vista IP Law Group LLP (57) ABSTRACT

Interelectrode impedance or electric field potential measurements are used to determine the relative orientation of one lead to other leads in the spinal column or other body/tissue location. Interelectrode impedance is determined by measuring impedance vectors. The value of the impedance vector is due primarily to the electrode-electrolyte interface, and the bulk impedance between the electrodes. The bulk impedance between the electrodes is, in turn, made up of (1) the impedance of the tissue adjacent to the electrodes, and (2) the impedance of the tissue between the electrodes. In one embodiment, the present invention makes both monopolar and bipolar impedance measurements, and then corrects the bipolar impedance measurements using the monopolar measurements to eliminate the effect of the impedance of the tissue adjacent the electrodes. The orientation and position of the leads may be inferred from the relative minima of the corrected bipolar impedance values. These corrected impedance values may also be mapped and stored to facilitate a comparison with subsequent corrected impedance measurement values.

20 Claims, 9 Drawing Sheets

(56) References Cited

U.S. PATENT DOCUMENTS

| | | |
|---|---|---|
| 4,539,640 A | 9/1985 | Fry et al. |
| 4,735,204 A | 4/1988 | Sussman et al. |
| 4,911,174 A | 3/1990 | Pederson et al. |
| 5,184,624 A | 2/1993 | Brown et al. |
| 5,201,865 A | 4/1993 | Kuehn |
| 5,333,618 A | 8/1994 | Lekhtman et al. |
| 5,702,429 A | 12/1997 | King |
| 5,722,402 A | 3/1998 | Swanson et al. |
| 5,735,887 A | 4/1998 | Barreras, Sr. et al. |
| 5,814,092 A | 9/1998 | King |
| 5,876,336 A | 3/1999 | Swanson et al. |
| 5,895,416 A | 4/1999 | Barreras, Sr. et al. |
| 5,913,882 A | 6/1999 | King |
| 5,941,906 A | 8/1999 | Barreras, Sr. et al. |
| 5,964,796 A * | 10/1999 | Imran ............ 607/122 |
| 6,027,456 A | 2/2000 | Feler et al. |
| 6,038,468 A * | 3/2000 | Rex ............ 600/424 |
| 6,052,624 A | 4/2000 | Mann |
| 6,106,460 A | 8/2000 | Panescu et al. |
| 6,181,969 B1 | 1/2001 | Gord |
| 6,353,762 B1 | 3/2002 | Baudino et al. |
| 6,393,325 B1 | 5/2002 | Mann et al. |
| 6,516,227 B1 | 2/2003 | Meadows et al. |
| 6,587,724 B2 | 7/2003 | Mann |
| 6,609,029 B1 | 8/2003 | Mann et al. |
| 6,640,119 B1 * | 10/2003 | Budd et al. ............ 600/374 |
| 6,662,053 B2 | 12/2003 | Borkan |
| 6,741,892 B1 | 5/2004 | Meadows et al. |
| 6,913,763 B2 | 7/2005 | Lerner |
| 6,993,384 B2 | 1/2006 | Bradley |
| 2003/0139781 A1 | 7/2003 | Bradley et al. |
| 2004/0049235 A1 | 3/2004 | Deno et al. |
| 2004/0078067 A1 | 4/2004 | Thompson et al. |
| 2004/0082978 A1 | 4/2004 | Harrison et al. |
| 2004/0116978 A1 | 6/2004 | Bradley |
| 2004/0172083 A1 | 9/2004 | Penner |
| 2006/0122653 A1 | 6/2006 | Bradley et al. |
| 2008/0125833 A1 | 5/2008 | Bradley et al. |

OTHER PUBLICATIONS

Office Action dated Nov. 14, 2008 for U.S. Appl. No. 11/342,989, filed Jan. 30, 2006, inventor: Kerry Bradley, (14 pages).
Office Action dated May 14, 2009 for U.S. Appl. No. 11/342,989, filed Jan. 30, 2006, inventor: Kerry Bradley, (8 pages).
Advisory Action dated Aug. 7, 2009 in U.S. Appl. No. 11/342,989, filed Jan. 30, 2006, inventor: Kerry Bradley, (3 pages).
Notice of Allowance dated Nov. 10, 2005 in U.S. Appl. No. 10/310,202, filed Dec. 3, 2002, inventor: Kerry Bradley, (4pages).
Notice of Allowance dated Dec. 1, 2009 in U.S. Appl. No. 11/342,989, filed Jan. 30, 2006, inventor: Kerry Bradley, (4pages).
Office Action dated Dec. 24, 2009 in U.S. Appl. No. 11/938,490, filed Nov. 12, 2007, inventor: Kerry Bradley, (18 pages).

* cited by examiner

| IMPEDANCE VECTOR | DISTANCE IMPEDANCE |
|---|---|
| BI_e1E5 | 300.3 |
| BI_e1E6 | 276.1 |
| BI_e1E7 | 87.8 |
| BI_e1E8 | 246.8 |
| BI_e2E5 | 301.8 |
| BI_e2E6 | 300 |
| BI_e2E7 | 217.3 |
| BI_e2E8 | 84.1 |
| BI_e3E5 | 342.5 |
| BI_e3E6 | 339.6 |
| BI_e3E7 | 290.4 |
| BI_e3E8 | 278.7 |
| BI_e4E5 | 327.3 |
| BI_e4E6 | 332.6 |
| BI_e4E7 | 289.4 |
| BI_e4E8 | 291.3 |

APPARATUS AND METHOD FOR DETERMINING THE RELATIVE POSITION AND ORIENTATION OF NEUROSTIMULATION LEADS

The present is a continuation of U.S. application Ser. No. 10/310,202, filed Dec. 3, 2002, to be issued on Jan. 31, 2006 as U.S. Pat. No. 6,993,384, which application claims the benefit of U.S. Provisional Patent Application Ser. No. 60/338,331, filed Dec. 4, 2001, each of which is incorporated herein by reference.

BACKGROUND OF THE INVENTION

The present invention relates to neurostimulation systems, such as a spinal cord stimulation (SCS) system, and more particularly to a method for determining the relative position and orientation of electrodes on a neurostimulation lead or leads used with such a system.

In SCS systems, positioning of the leads is critical to the success of the therapy. During surgery, the physician places the leads in a very careful manner in order to locate the electrodes proximal to neural elements that are the target of the stimulation. During and after placement, stimulation energy is delivered to verify that the leads are indeed stimulating the appropriate neural elements.

However, if the leads happen to shift position, the targeted neural elements may no longer be appropriately stimulated. At best, this can require electrical reprogramming to restore therapy or, at worst, surgical revision, where a second surgery is required and the leads must be manually readjusted. In the first case, the physician may have only a suspicion that a lead has shifted position, based on patient reporting of paresthesia, which is not foolproof. Also, attempting to reprogram the leads based on paresthesia locations can be challenging.

What is needed is a more objective technique for verifying the position of the leads.

Prior art approaches for determining the lead position are disclosed in U.S. Pat. Nos. 4,486,835; 4,539,640; and 5,184,624, which patents are incorporated herein by reference.

SUMMARY OF THE INVENTION

The present invention addresses the above and other needs by providing a cross-check technique for verifying the position of the electrodes of the implanted leads. A first technique involves the use of interelectrode impedance. A second technique involves measured field potentials. Either technique advantageously allows the relative orientation of one electrode on an implanted lead to other electrodes on the implanted lead or adjacent implanted leads in the spinal column or other body/tissue location to be readily determined. Such techniques are useful not only for reprogramming, but also to estimate if the shifted orientation of the electrodes is sufficiently large so as to make electrical reprogramming a waste of time, thereby suggesting that surgery may need to be performed for repositioning.

At present, the correct lead position may only be determined by X-ray or fluoroscopy. Disadvantageously, X-ray and fluoroscopy require expensive equipment, significant time, and appropriate medical facilities, most of which are not readily available.

The general process for fitting a neurostimulation patient, i.e, a spinal cord stimulation patient, is described, e.g., in U.S. Pat. Nos. 6,052,624; 6,393,325; in published international patent application WO 02/09808 A1 (published 7 Feb. 2002); and in U.S. patent applications (assigned to the same assignee as the present application) Ser. No. 09/626,010, filed Jul. 26, 2000; and Ser. No. 09/740,339, filed Dec. 18, 2000, which patents, publication, and applications are incorporated herein by reference. As indicated in those documents, prior to fitting a patient with the certain types of neurostimulation leads, the relative orientation of the electrodes on the implanted leads should be known in order to allow appropriate navigation of the stimulation energy. At present, a determination of the relative orientation typically requires that a fluoroscope or X-ray image of the implanted leads be present at the time of patient setup with the system programmer. Disadvantageously, however, such images may not always be available. Moreover, between the time of implant and follow-up visits, the leads may have shifted and the fluoroscope image may no longer be valid. This can result in poor patient outcomes due to inappropriate or unexpected stimulation effects during fitting.

Hence, it is seen that there is a need for the cross-check techniques provided by the present invention, which techniques can be used to verify the position of the leads at numerous times during the lifetime of the implanted leads, e.g., during initial implantation and programming, during followup visits, throughout the trial period, and during subsequent reprogramming sessions.

BRIEF DESCRIPTION OF THE DRAWINGS

The aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claim(s).

The present invention uses: (1) interelectrode impedance (one technique or embodiment) or (2) measured field potentials (another technique or embodiment) to determine the relative orientation of one electrode on an implanted lead to other electrodes on the implanted lead or adjacent implanted leads in the spinal column or other body/tissue location.

Figure 1:
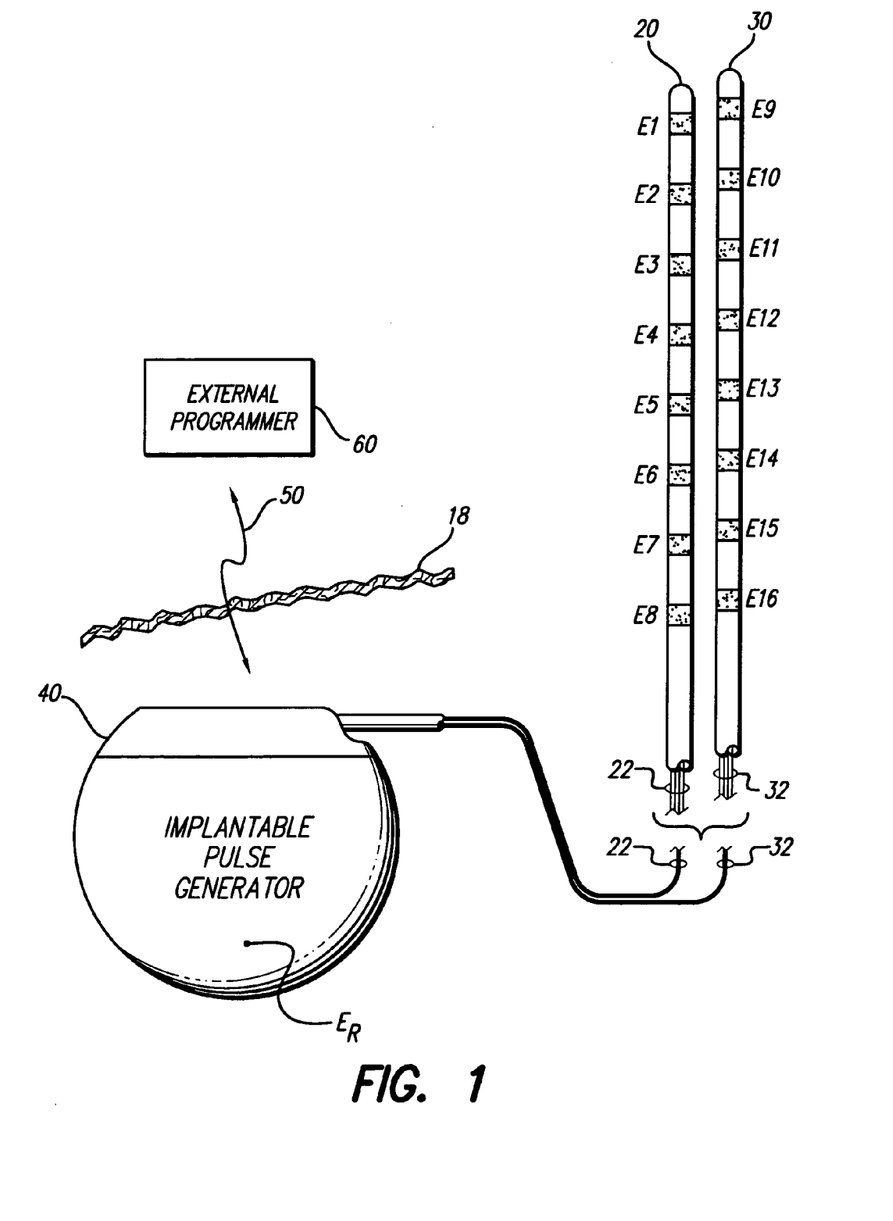
FIG. 1 illustrates a neurostimulation system wherein two leads, each having eight in-line electrodes thereon, are positioned side-by-side, and wherein each lead is connected to an implantable pulse generator (IPG), which IPG is, in turn, coupled to an external programmer.

Before describing the two techniques, either of which may be used, it will be helpful to first briefly provide an overview of a representative neurostimulation system of the type with which the present invention may be used. A representative neurostimulation system is illustrated in FIG. 1. Such system may include a first implantable lead 20 and a second implantable lead 30. Each lead includes a series of in-line electrodes thereon. For the example shown in FIG. 1, the first lead 20 contains eight in-line electrodes E1, E2, E3, . . . E8. The second lead 30 also contains eight in-line electrodes E9, E10, E11, . . . . E16.

Each of the electrodes of each lead 20 or 30 are electrically connected through respective wires, embedded or carried within a body of the lead, to an implantable pulse generator (IPG) 40. The wires connected to the electrodes E1, E2, E3, . . . . E8 of lead 20, for example, may be characterized as a bundle of wires 22 that are electrically connected with the IPG 40. Similarly, the wires connected to the electrodes E9, E10, E11, . . . . E16 of lead 30 may be characterized as a bundle of wires 32 that are electrically connected with the IPG 40. Through these wires, carried within the respective leads 20 or 30, the IPG is able to direct electrical stimulation to selected electrodes of each lead.

When a given electrode is selected to receive an electrical stimulus, it is (for purposes of the present invention) said to be "activated". When an electrode is not selected to receive an electrical stimulus, it is said to be "non-activated". Electrical stimulation must always occur between two or more electrodes (so that the electrical current associated with the stimulus has a path from the IPG to the tissue to be stimulated, and a return path from the tissue to the IPG). The case of the IPG may function, in some modes of operation, as a return electrode ER. Monopolar stimulation occurs when a selected one of the electrodes of one of the leads 20 or 30 is activated along with the return electrode ER. Bipolar stimulation occurs when two of the electrodes of the leads 20 or 30 are activated, e.g., when electrode E3 of lead 20 is activated as an anode at the same time that electrode E11 of lead 30 is activated as a cathode. Tripolar stimulation occurs when three of the electrodes of the leads 20 or 30 are activated, e.g., when electrodes E4 and E5 of lead 20 are activated as an anode at the same time that electrode E13 of lead 30 is activated as a cathode. In general, multipolar stimulation occurs when multiple electrodes of the leads 20 or 30 are activated.

The IPG 40 is typically programmed, or controlled, through the use of an external (non-implanted) programmer 60. The external programmer 60 is coupled to the IPG 40 through a suitable communications link, represented in FIG. 1 by the wavy arrow 50. Such link 50 passes through the skin 18 of the patient. Representative links that may be used to couple the programmer 60 with the IPG 40 include a radio frequency (RF) link, an inductive link, an optical link, or a magnetic link. The programmer 60, or other similar external device, may also be used to couple power into the IPG for the purpose of operating the IPG or charging a replenishable power source, e.g., a rechargeable battery, within the IPG. Once the IPG 40 has been programmed, and its power source has been fully charged or replenished, it may operate as programmed without the need for the external programmer 60 to be present.

Figure 2:
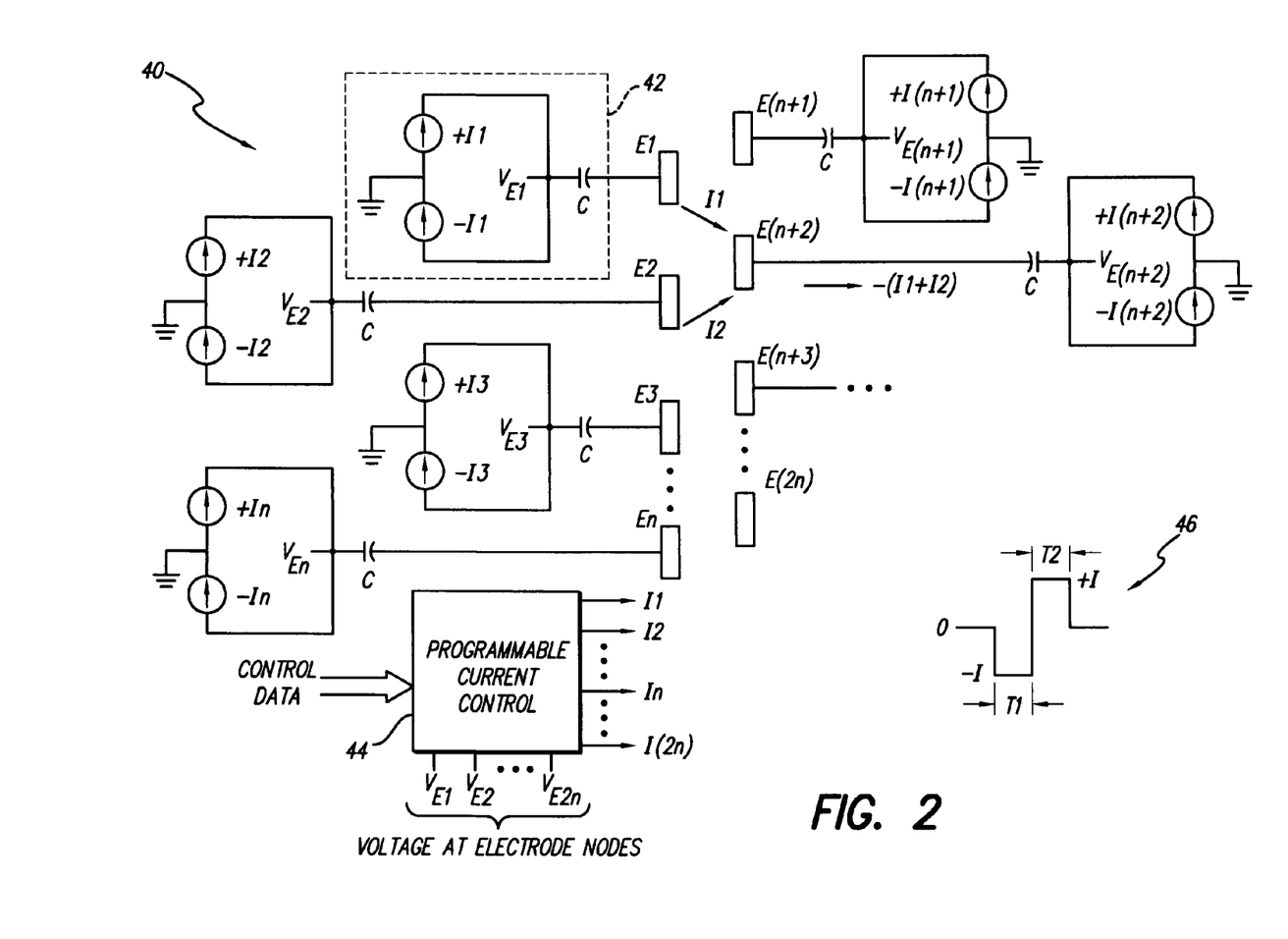
FIG. 2 shows a functional block diagram of an IPG that uses multiple programmable current sources to activate selected electrodes of the neurostimulation leads.

Turning next to FIG. 2, there is shown a representative functional block diagram of one type of IPG 40 that may be used with a neurostimulation system. As seen in FIG. 2, the IPG 40 therein depicted is made up of a multiplicity of dual current sources 42. Each dual current source 42 includes a positive current source, i.e., a current source that can function as an anode to "source" current to a load, and a current source that can function as a cathode to "sink" current from a load through the same node. The "load" is the tissue that resides between the two or more activated electrodes, and includes the wire (or other conductive element) and a coupling capacitor C that connects the electrode to the common node of the dual current source.

Thus, for example, and as depicted in FIG. 2, a first dual current source connected to electrode E1 of a first lead through a coupling capacitor C, may be programmed to produce a current of +I1 or −I1 through electrode E1, depending upon whether such dual current source is configured to operate as a cathode or an anode, when such first dual current source is turned on or enabled. Similarly, a second current source, connected to electrode E2, when turned on or enabled, may be programmed to produce a current of +I2 or −I2 through electrode E2. In a similar manner, a third current source, when enabled, may be programmed to produce a current of +I3 or −I3 through electrode E3. An nth current source, where n represents the number of electrodes on the first lead, is similarly connected to electrode En, and may be programmed to produce a current of +In or −In through electrode En when turned on or enabled.

If a second lead, also having n electrodes, is positioned adjacent the first lead, each electrode is similarly connected to a dual current source. For example, electrode E(n+1) is connected to a dual current source that produces a current of +I(n+1) or −I(n+1) through electrode E(n+1) when such (n+1)th current source is enabled. In like manner, all of the electrodes of the second lead are connected to respective dual current sources. There are thus 2n dual current sources that are respectively connected to each of the 2n electrodes of the first and second leads (n electrodes on each lead). Alternative embodiments (not shown) may employ less than 2n dual current sources connected to 2n electrodes through a suitable multiplexer circuit.

A programmable current control circuit 44 is also provided within the IPG 40 that controls, i.e., turns on or enables, at specified times, a selected current source to operate as either a cathode or an anode to source or sink a current having a desired amplitude. The control circuit 44 also disables, or turns off, selected current sources, as controlled by programmed control data received from the external programmer, or otherwise resident within the IPG. The control circuit 44 further includes the ability to measure the electrode voltage, $E_{V1}, E_{V2}, E_{V3}, \ldots E_{Vn}, \ldots E_{V(2n)}$, appearing at the output of each dual current source 42, whether the electrode is activated or non-activated. This effectively allows the electrode voltage, or electric field at the electrode, to be measured, which in turn facilitates impedance or field potential measurements to be made, which measurements are used in carrying out various steps of the invention as described below.

Thus, in operation, and as illustrated in FIG. 2, current control circuit 44 may turn on current sources +I1 and +I2 at the same time, i.e., during a time period T1, that current source −I(n+2) is turned on. All other current sources are turned off, or disabled, during the time T1. Such action causes electrodes E1 and E2 to be activated as anodes at the same time that electrode E(n+2) is activated as a cathode. That is, a current +I1 is "sourced" from electrode E1 and a current +I2 is "sourced" from electrode E2 at the same time that a current −I(n+2) is "sunk" into electrode E(n+2). The amplitudes of the currents +I1 and +I2 may be any programmed values, and the amplitude of the current −I(n+2) should be equal to −(I1+I2). That is, the current that is sourced is equal to the current that is sunk.

After the time period T1, it is common to switch the polarities of the electrodes during a second time period T2. During T2, the electrodes E1 and E2 are activated as cathodes, so that they both sink current, and electrode E(n+2) is activated as an anode, so that it sources a current equal in amplitude to the current that is sunk by electrodes E1 and E2. In this manner, a biphasic stimulation pulse 46 is produced that is characterized by a first pulse (during time period T1) of one polarity, followed by a second pulse immediately or shortly thereafter (during time period T2) of the opposite polarity. The electrical charge associated with the first pulse is made so that it is equal to the charge associated with the second pulse, thereby maintaining charge balance during the stimulation. (Maintaining charge balance when stimulating living tissue is generally considered an important component of a stimulation regime.) Charge balance is commonly achieved in a biphasic pulse 46 by making the amplitude of the first pulse during time T1 equal to the amplitude of the second pulse during time period T2, where T1 equals T2. However, charge balance may also be achieved using other combinations of pulse duration and amplitude, e.g., by making the amplitude of the second pulse equal to ½ the amplitude of the first pulse, while making the time period T2 equal to twice the time period T1.

Figure 3:
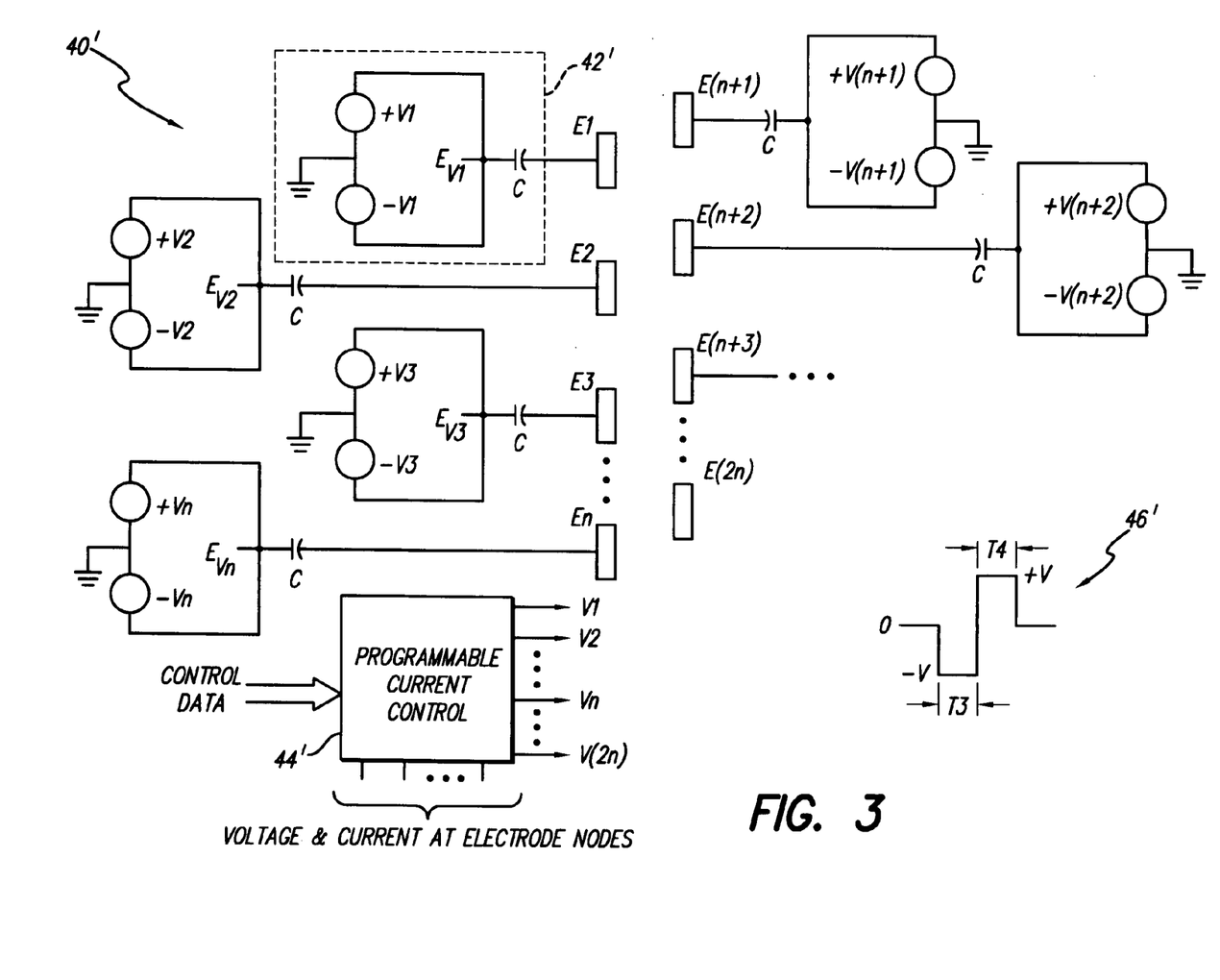
FIG. 3 shows a functional block diagram of an IPG that uses multiple programmable voltage sources to activate selected electrodes of the neurostimulation leads.

Next, with respect to FIG. 3, a functional block diagram of another type of IPG 40' that may be used in a neurostimulation system is shown. The IPG 40' shown in FIG. 3, includes a multiplicity of dual voltage sources 42', each being connected to one of the electrodes E1, E2, E3, . . . . En, of a first lead, or to one of the electrodes E(n+1), E(n+2), . . . E(2n), of a second lead. Each dual voltage source 42' applies a programmed voltage, of one polarity or another, to its respective electrode, when enabled or turned on. For the configuration shown in FIG. 3, a separate dual voltage source 42' is connected to each electrode node through a coupling capacitor C. (Other embodiments, not shown, may use one or two or more voltage sources that are selectively connected to each electrode node through a multiplexer circuit.)

The control circuit 44', or other circuitry within the IPG 40', further includes the ability to measure the electrode current, $E_{I1}, E_{I2}, E_{I3}, \ldots E_{In}, \ldots E_{I(2n)}$, flowing to or from its respective electrode, whether the electrode is activated or non-activated, and the electrode voltage, $E_{V1}, E_{V2}, E_{V3}, \ldots E_{Vn}, \ldots E_{V(2n)}$, appearing at the output of each non-activated dual voltage source 42' These measurements facilitate impedance and electric field measurements or calculations to be made, which measurements are used in carrying out various steps of the invention as described below.

A programmable voltage control circuit 44' controls each of the dual voltage sources 42', specifying the amplitude, polarity, and duration of the voltage that is applied to its respective terminal. Typically, stimulation is achieved by applying a biphasic stimulation pulse 46' to the selected electrodes, wherein a voltage of a first polarity and amplitude is applied during time period T3, followed by a voltage of the appositive polarity and amplitude during time period T4. The biphasic stimulation pulse 46' may be applied between any two or more electrodes.

It should be noted that the functional block diagrams of FIGS. 2 and 3 are functional diagrams only, and are not intended to be limiting. Those of skill in the art, given the descriptions presented herein, should be able to readily fashion numerous types of IPG circuits, or equivalent circuits, that carry out the functions indicated and described, which functions include not only producing a stimulus current or voltage on selected groups of electrodes, but also the ability to measure the voltage, or the current, flowing through an activated or non-activated electrode. Such measurements allow impedance to be determined (used with a first embodiment of the invention) or allow electric field potentials to be measured (used with a second embodiment of the invention), as described in more detail below. A preferred IPG is described in international patent application WO 02/09808 A1 (published 7 Feb. 2002); and in U.S. patent application Ser. No. 09/626,010, filed Jul. 26, 2000, which publication and application have been previously referenced and are incorporated herein by reference.

With the descriptions of FIGS. 1-3 thus providing background information relative to a neurostimulation system, the present invention will next be described. As has been indicated, the present invention addresses the problem of determining the relative position between electrodes once the leads on which the electrodes are carried have been implanted. The present invention uses: (1) interelectrode impedance (one technique or embodiment) or (2) measured field potentials (another technique or embodiment) to determine the relative orientation of one electrode on an implanted lead to other electrodes on the implanted lead or adjacent implanted leads in the spinal column or other body/tissue location.

First, the interelectrode impedance technique of the invention will be explained in connection with FIGS. 4-6. The interelectrode impedance technique is performed by measuring impedance vectors. A vector is defined as an impedance value measured between two electrodes in the body. The value of the impedance vector is due primarily to two physical entities:

(1) the electrode-electrolyte interface; and
(2) the bulk impedance between the electrodes.

The impedance tomography technique of the present invention relies upon the latter of the above two physical entities, i.e., upon the bulk impedance between the electrodes.

The bulk impedance portion of the impedance vector may be further broken up into two contributing factors: (a) the impedance of the tissue adjacent to the electrodes; and (b) the impedance of the tissue between the electrodes.

The first factor (part a) makes up the majority of the measurement, due to the higher and non-uniform current densities near the electrode surface. However, the second factor (part b), where the current density is more uniform, has a roughly linear relationship to distance between the two electrodes, due to the definition of resistance. Resistance, R, is defined as R=(resistivity)×(distance)/cross-sectional area.

The second factor (part b) is used by the interelectrode impedance technique embodiment of the invention to determine the relative spacing between electrodes and to determine the relative orientation of the leads.

Figure 5:
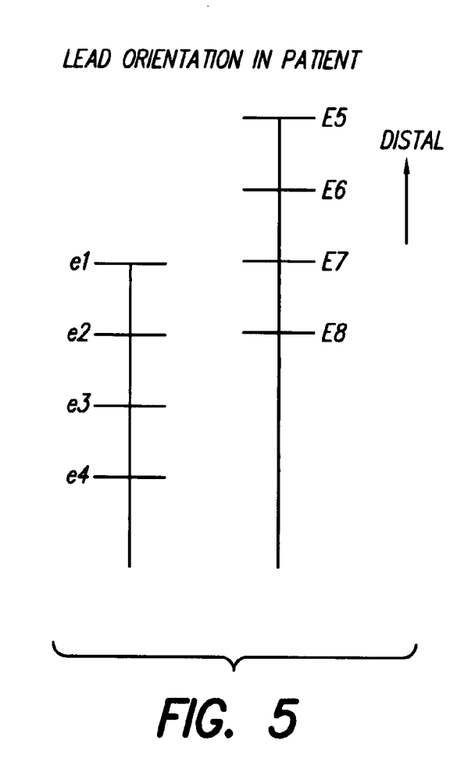
FIG. 5 illustrates representative relative electrode orientation in a patient having dual quadrapolar leads (two side-by-side leads, each having four in-line electrodes thereon)
Figure 6:
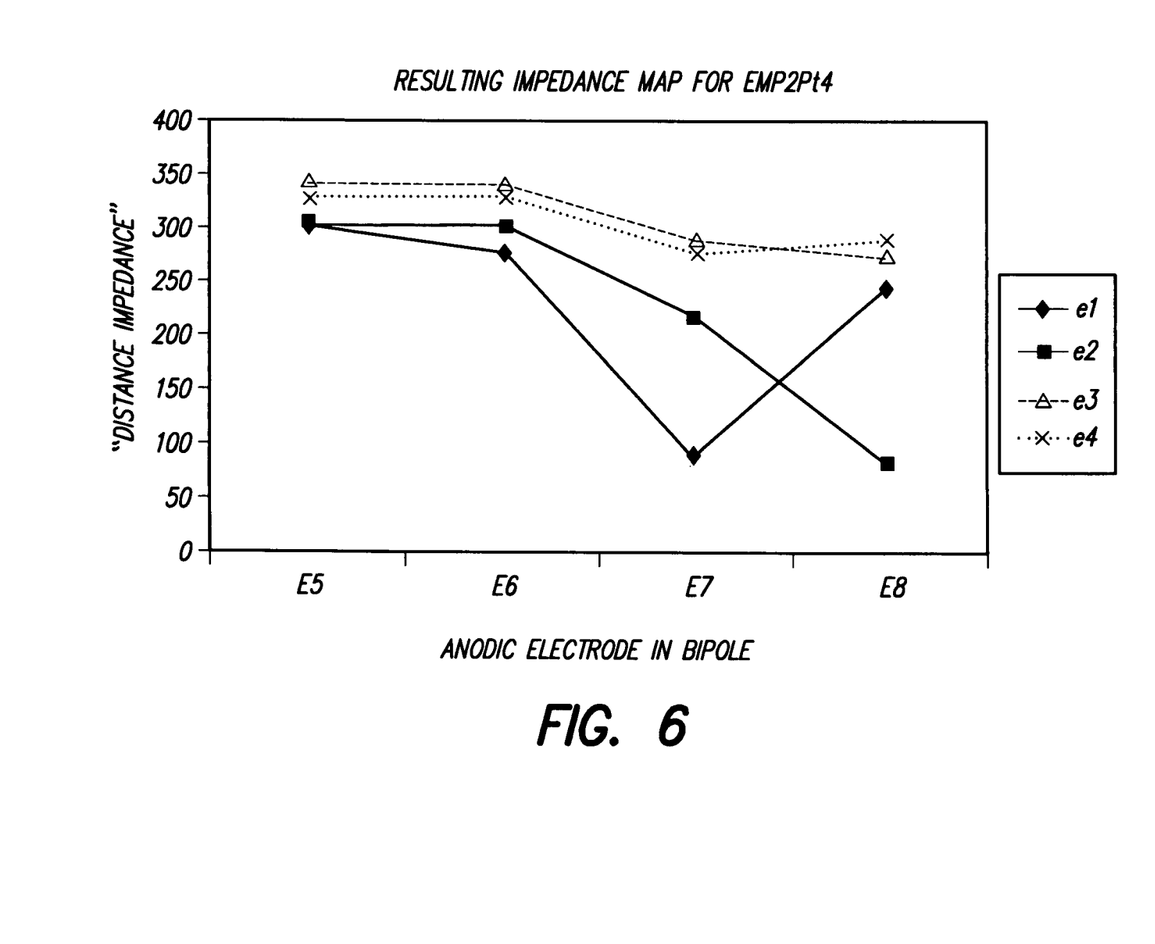
FIG. 6 is an impedance map that illustrates application of one embodiment of the invention to the electrode orientation shown in FIG. 5.

By way of example, one first-order, simple embodiment of the invention is as follows:

If two multipolar leads are placed in the spinal column, see FIG. 5, each having four electrodes (the electrodes of one lead being designated as e1, e2, e3, and e4; and the electrodes of the other lead being designated as E5, E6, E7 and E8), their relative orientation may be inferred by making the following measurements:

1. Monopolar impedances for all electrodes; and
2. Bipolar impedances between each electrode on opposing leads.

The monopolar impedances are used to "correct" the bipolar impedances for the first factor of bulk impedance, the strongly-weighted impedance near the electrode. The corrected bipolar impedances are then used to develop an impedance "map" between the electrodes. This map reveals the relative orientation of the leads.

To illustrate, a sample correction formula is as follows:

(distance between two electrodes e1 & e2)≈(measured bipolar impedance between two electrodes e1 & e2)+(2*offset)−(monopolar Z for electrode e1)−(monopolar Z for electrode e2), where offset=an estimate of the impedance in the monopolar impedance measurement that is NOT due to the tissue near the electrode.

After the bipolar impedances are corrected by the above formula, the relative orientation of the leads may be inferred by the relative minima of the impedance values. Where the corrected bipolar impedance between two electrodes is a minimum relative to other electrodes on an opposing array, those electrodes are relatively adjacent. This information may then be loaded into a programmer, which can then provide a graphic display of the assumed relative lead positions. Such data and/or display might then be compared with previously measured or entered and stored graphics, indicating earlier orientations. Such comparison can thus help the physician/clinician to track the lead orientation to determine appropriate programming, reprogramming, or need for surgical revision.

Also, for some programming systems, the present invention may be used to automatically setup the appropriate navigation tables for steering multiple lead systems.

Figure 4:
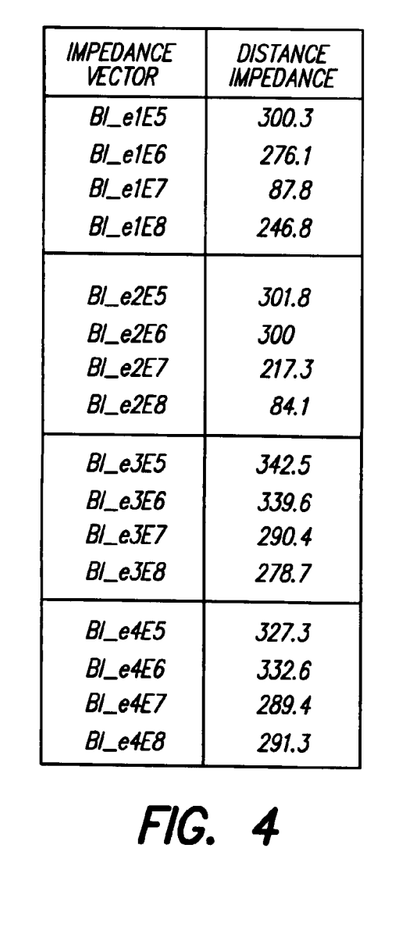
FIG. 4 is a table that contains impedance vector and distance impedance data in accordance with one embodiment of the invention.

FIG. 4 illustrates data showing this simple embodiment applied to data from a patient with dual quadrapolar leads, which leads are oriented as depicted in FIG. 5. FIG. 6 shows the impedance map resulting from the measurements of FIG. 4. It can be seen that the impedance maps (FIG. 6) correlate well to the orientation of the leads (FIG. 5).

The simple interelectrode impedance technique described above may be enhanced by making more accurate corrections using the appropriate field equations to calculate the monopolar and bipolar impedance of the electrodes. Also, other geometric methods may be employed using the improved "distance impedance" values to improve the mapping of the electrode orientations.

Next, an alternative technique or embodiment for determining relative electrode positions for multipolar leads of a neurostimulation system will be described. Such alternative technique utilizes electric field measurements of the implanted electrodes, and more particularly, electric field measurements on non-active electrodes caused by activation of other electrodes. In a preferred embodiment of this alternative embodiment, a constant current is sourced (anodes) and sunk (cathodes) from a predefined combination of electrodes. Such electrodes thus comprise the activated electrodes. Then, the resulting potentials are measured at all other electrodes (those not involved in sourcing or sinking current), i.e., the non-activated electrodes. From these measured potentials, the relative orientation of the electrodes, and the leads on which the electrodes are carried, may be determined. Advantageously, the use of field potentials represents an improvement over the use of impedance measurements, since the measured potential values are less subject to the confounding effects of the tissue impedance very close to the source/sink electrodes.

Figure 7:
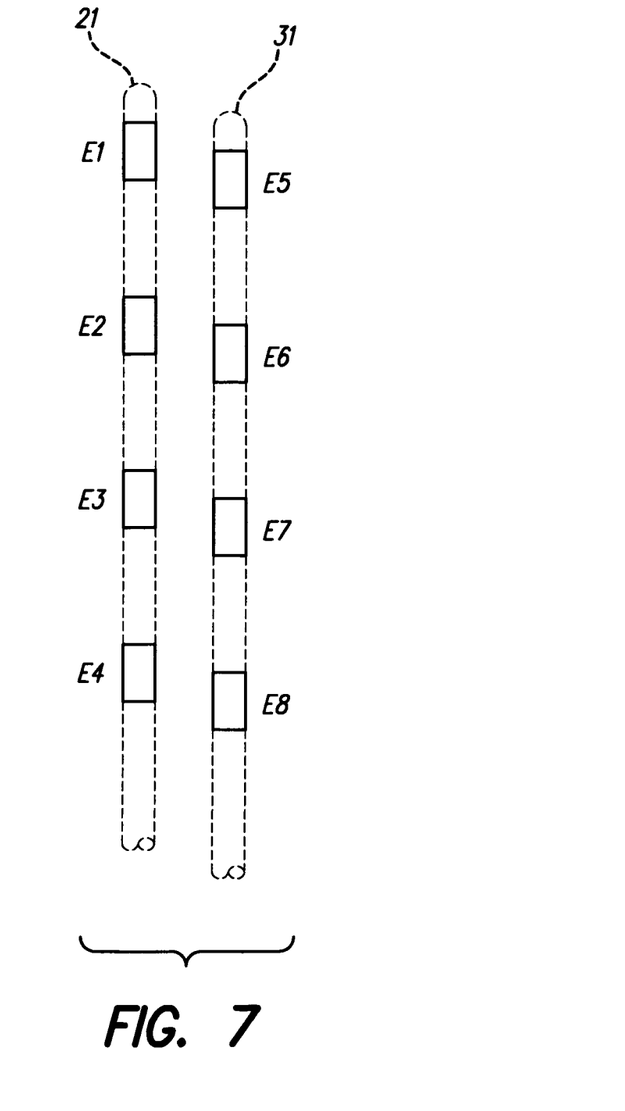
FIG. 7 depicts a representative fluoroscopic image of dual quadrapolar leads in a patient.
Figure 8:
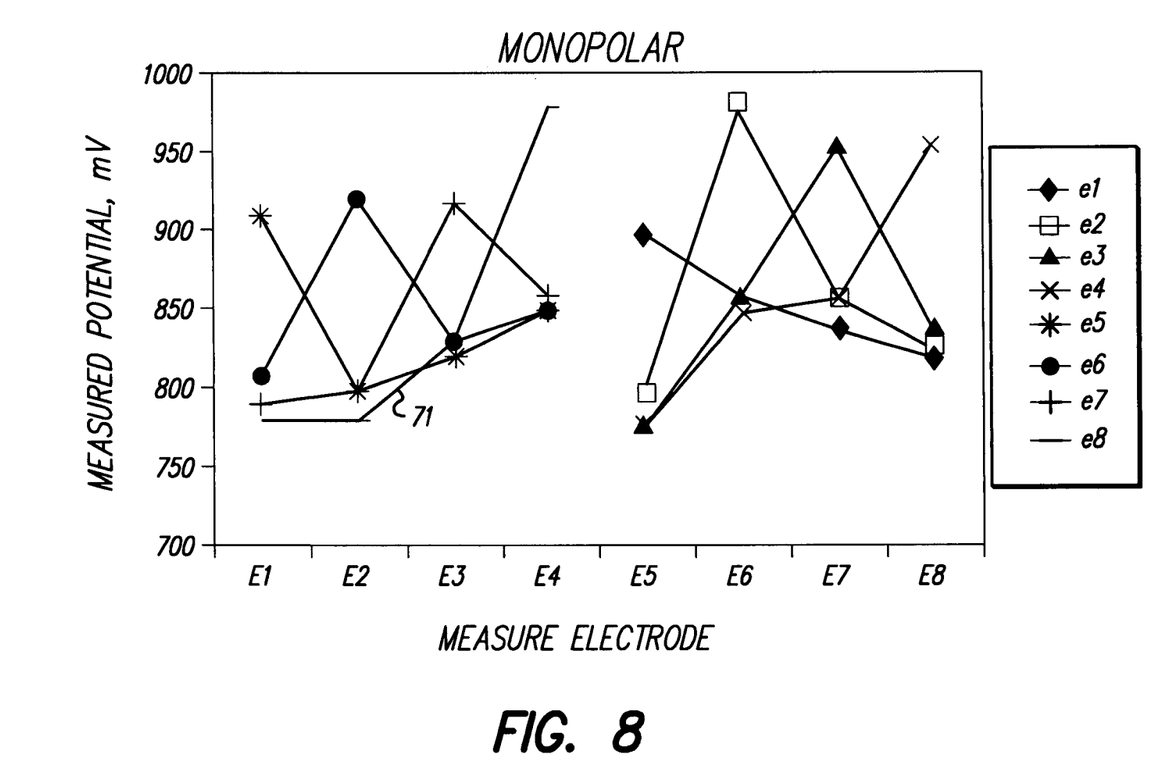
FIG. 8 illustrates, in accordance with another embodiment of the invention, the measured electrode potential of non-activated electrodes on the dual quadrapolar lead of FIG. 7 when the activated electrode is activated through monopolar stimulation.
Figure 9:
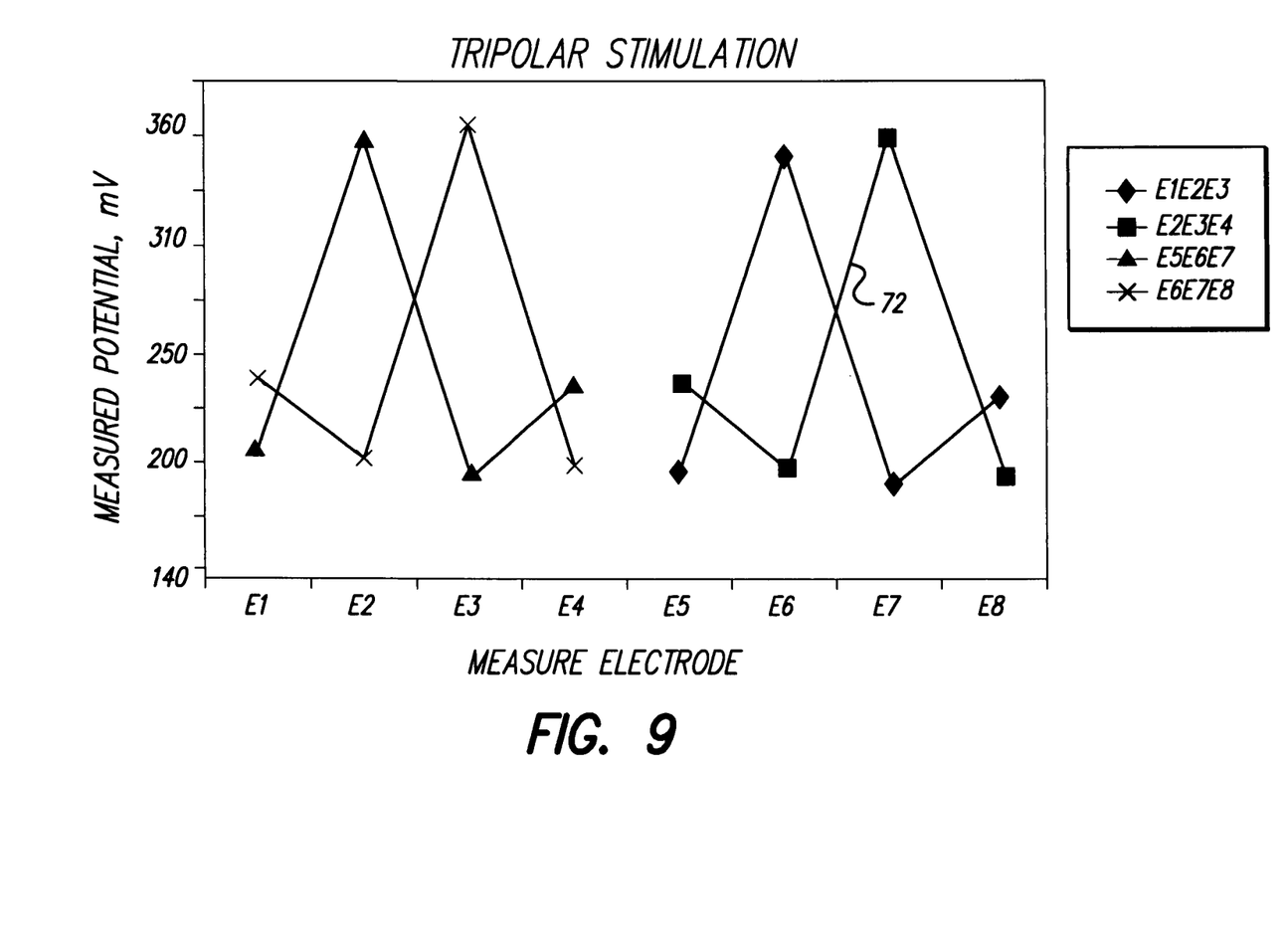
FIG. 9 illustrates the measured electrode potential of non-activated electrodes on the dual quadrapolar lead of FIG. 7 when the activated electrodes are activated through tripolar stimulation.

By way of example of this electric field potential measurement technique, consider FIGS. 7, 8 and 9. FIG. 7 represents the relative position of dual quadrapolar leads 21 and 31 after being implanted in a patient, as obtained using a fluoroscopic imaging device. In many instances, the necessary imaging equipment needed to obtain a fluoroscopic image, such as is shown in FIG. 7, is not readily available. Advantageously, the present electrical field potential measurement technique represents an alternative approach to obtaining relative electrode position information rather than using an expensive and cumbersome imaging device.

Two combinations of anodes/cathodes are used to deliver current to the leads of the dual quadrapolar leads 21 and 31. The first technique is monopolar (current delivered or sourced from one electrode—the cathode—and sunk to the return electrode $E_R$—the anode). Thus, for each active monopolar combination, there are seven non-active electrodes on which the electric field may be measured. The second technique is flanked tripolar stimulation (current delivered between two anodes and one cathode, with the cathode being flanked on each side by an anode).

In both the monopolar stimulation and the tripolar stimulation, a constant current is delivered to each electrode implanted in the patient's body while the electric field potential is measured on all other electrodes NOT involved in sinking/sourcing current. The constant current may be set to a subperception level, or to another suitable level that is comfortable for the patient.

The electric field potentials for the monopolar stimulation are plotted on the same chart in FIG. 8. The vertical axis is millivolts. As seen in FIG. 8, the electrodes closest to the source electrode have a high potential (note: all plots in FIG. 8 and FIG. 9 are "negative", i.e., more negative potentials results in more positive measured values, as shown in the plots). Thus, for example, consider electrode E8 (curve 71), which has its highest potential relative to electrode E4, and its lowest potential relative to electrodes E1 and E2, and an intermediate potential relative to electrode E3. This corresponds to the actual electrode positions shown in FIG. 7, where electrode E8 is closest to electrode E4, somewhat further from electrode E3, and farthest from electrodes E2 and E1. A similar analysis for the monopolar stimulation fields of the other electrodes reveals a similar relationship: the electrodes closest to the source electrode have the higher potential.

The electric field potentials for the tripolar stimulation are plotted on the same chart in FIG. 9. Again, the vertical axis is millivolts. As seen in FIG. 9, a better relative orientation can be obtained than can be obtained with the monopolar stimulation. Those electrodes closest to the cathode have a high potential while those electrodes closest to the anode have a lower potential relative to the electrodes further away. For example, consider curve 72, which shows the electric field potential of the non-active electrodes relative to the tripolar stimulation of electrodes E2E3E4, with E2 and E4 being anodes, and E3 being a cathode. As seen in FIG. 9, curve 72 has a peak corresponding to electrode E7, which means electrode E7 is closest to the cathode E3. Curve 72 further has lows or valleys corresponding to electrodes E6 and E8, which means E6 and E8 are closest to anode electrodes E2 and E4. The actual orientation of the electrodes shown in FIG. 7 reveals that E6 is closest to E2, and E8 is closest to E4. Thus, it is seen that those electrodes closest to the flanked cathodic electrode have a high potential while those electrodes closest to the anodic electrodes, on either side of the cathodic electrode, have a lower potential relative to the electrodes further away.

Hence, it is seen that by measuring the potential field of the non-active electrodes, when active electrodes are stimulated at constant current levels, e.g., subperception levels, the relative orientation of the neurostimulation leads may be determined. Once known, the relative orientation may be used to track lead migration, to setup stimulation configurations and parameters for nominal stimulation and/or navigation, and to automatically adjust stimulation energy to a previously-defined optimal potential field in the case of lead migration or postural changes.

Figure 10:
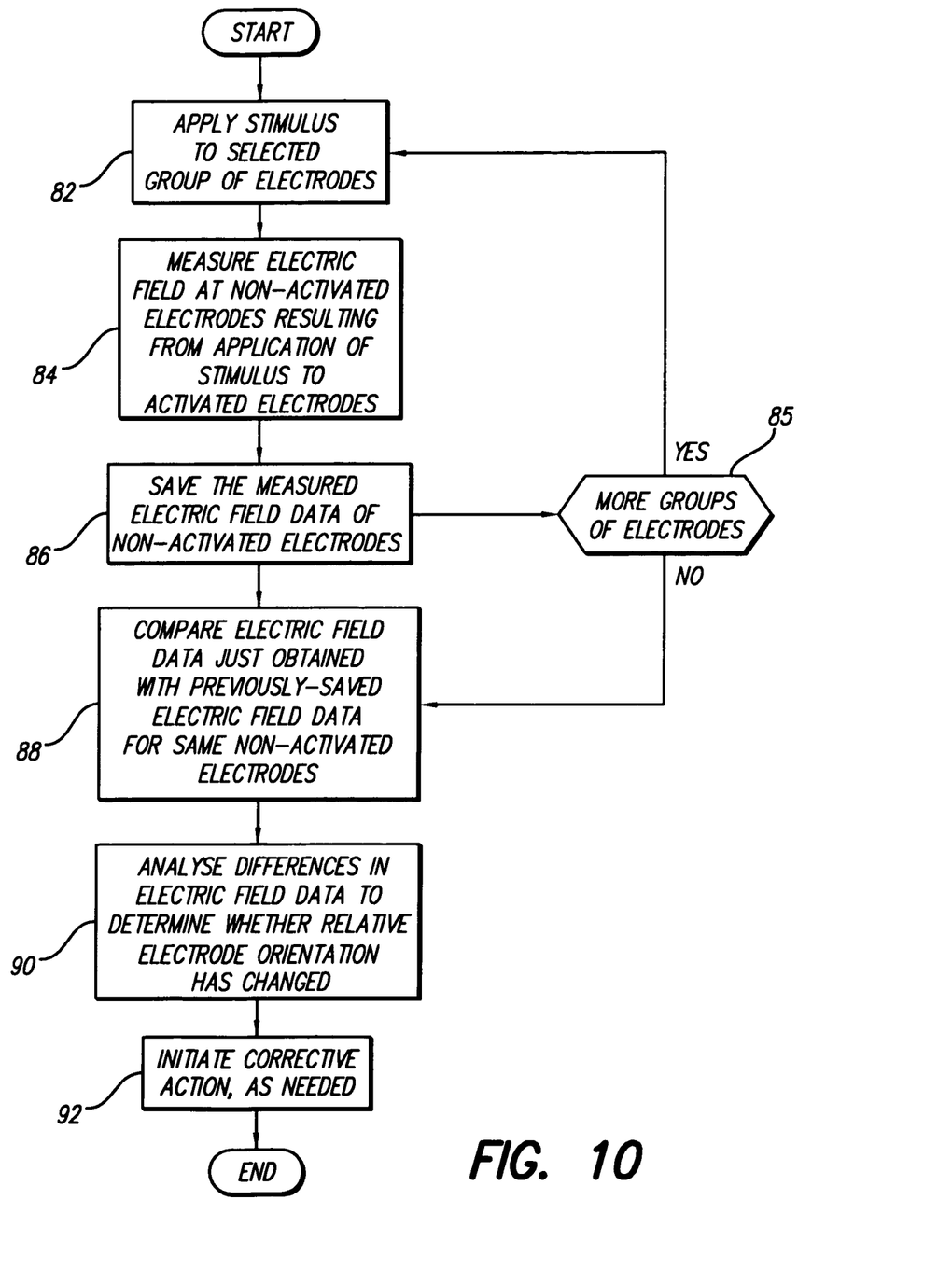
FIG. 10 is a flowchart that highlights the main steps used with one embodiment of the present invention.

Next, with reference to FIG. 10, a flowchart is shown that illustrates the main steps that may be used to carry out and apply the invention described above in connection with FIGS. 7-9. As seen in FIG. 10, a first step involves applying suitable stimuli, e.g., subperception stimuli, to a selected group of electrodes (block 82). Such application of stimuli defines the activated electrodes. While the stimuli are being applied to the activated electrodes, the electric field at the non-activated electrodes is measured (block 84) and saved (block 86) as electric field data (Block 86). Then, a determination is made as to whether there are other groups of electrodes that should be the "activated" electrodes, so that additional electric field measurements can be made of the "non-activated" electrodes (block 85). If YES (there are more electrode groups), then the steps shown at blocks 82, 84, and 86 are repeated using the new group of activated electrodes. If NO (all the electrode groups have been used), then the electric field data just obtained is compared to previously-saved electric field data for the same non-activated electrodes (block 88).

The previously-saved electric field data may have been obtained during initial implantation of the leads, or during the last visit (several weeks or months ago) to the doctor. Or, the previously-saved electric field data may have been obtained just a new hours or minutes ago at a time when the patient's body had assumed a different posture position. Regardless of when the previously-saved electric field data was obtained, the purpose of the comparison performed at block 88 of FIG. 10 is to determine if the relative position of the leads has changed, which change in position would also have caused a relative change in the position of the electrodes carried on the leads. Such determination may be made by analyzing the electric field data (block 90) as described above in connection with FIG. 8 and/or FIG. 9 to determine whether the relative electrode orientation has changed.

The magnitude of the difference in the compared electric field data may advantageously provide a relative measure of how far the lead has shifted or moved since the last electric field data was obtained. Advantageously, once a determination has been made that the leads (electrodes) have shifted relative to each other, appropriate correction action may be taken, as needed (block 92).

The corrective action taken at block 92 of FIG. 10 may include, for example, simply tracking the lead migration over time, so that other corrective action, e.g., surgery to reposition the leads, can be taken when necessary. Even if new surgery to reposition the leads is not needed, simply mapping the lead migration overtime will enable reprogramming of the stimuli parameters as needed so that a desired effect can be obtained regardless of the lead movement.

The corrective action may further include setting up stimulation configurations and parameters for providing nominal stimulation suitable for the electrodes in their new relative positions. For example, the amplitude of the stimulus applied to one electrode may be decreased if it is determined that the electrode has migrated closer to another stimulating electrode of the same polarity during stimulation, thereby preserving approximately the same stimulation effect for the patient. Alternatively, the amplitude of the stimulus applied to the electrode may be increased if the electrode has migrated closer to a stimulating electrode of the opposite polarity. Such amplitude adjustments may be made manually or automatically, depending on the mode of operation of the neurostimulation system.

Yet another corrective action that may be taken at block 92 of FIG. 10 is to adjust the distribution of the stimuli to a new location through navigation. Navigation, as described in the previously referenced patent documents, involves electronically shifting the stimulus current from one group of electrodes to another so as to shift or move the location where the patient feels the most beneficial paresthesia, and/or receives the most benefit. Such navigation allows the neurostimulation system to be quickly "fitted" to a given patient. Fitting the neurostimulation system to the patient is necessary after the system is first implanted, and may also be necessary whenever the leads (electrodes) have moved. The present invention thus provides a relatively easy way to determine whether such lead movement has occurred, and thereby whether a refitting is or may be necessary.

Yet additional corrective action that may be taken at block 92 of FIG. 10 in response to a determination that lead migration or postural changes have occurred includes manually or automatically adjusting the stimulation energy to a previously-defined optimal potential field.

It is thus seen that the present invention uses a measure of impedance or electric field to determine relative lead positions for multipolar leads in a multi-lead configuration of a neurostimulation system, e.g., a spinal cord stimulation system.

It is also seen that the invention uses impedance or electric field measurements to determine relative lead positions, which impedance or electric field measurements may be used as an automated or assistive method for setting up a programmer for navigation, other programming, or diagnostic evaluations in spinal cord (or other neural) stimulation.

It is additionally seen that the invention may be directed to the storing of impedance or electric field maps to chronically track relative lead positions in a programmer linked to a database, along with other patient data.

While the invention herein disclosed has been described by means of specific embodiments and applications thereof, numerous modifications and variations could be made thereto by those skilled in the art without departing from the scope of the invention set forth in the claims.

What is claimed is:

1. A method, comprising:
   determining, using circuitry, a relative two-dimensional orientation of first and second multiple-electrode leads implanted within a user;
   conveying electrical stimulation energy from a pulse generator implanted within the user into tissue of the user via the first and second multiple-electrode leads; and
   displaying the relative two-dimensional orientation of the first and second multiple-electrode leads.

2. A method as claimed in claim 1, wherein determining the relative two-dimensional orientation of first and second multiple-electrode leads comprises measuring impedance vectors between lead electrodes and inferring the relative two-dimensional orientation of the leads by the relative minima of the impedance vectors.

3. A method as claimed in claim 1, wherein determining the relative two-dimensional orientation of the first and second multiple-electrode leads comprises measuring impedance vectors between respective electrode pairs that each include one of the electrodes on the first multiple-electrode lead and one of the electrodes on the second multiple-electrode lead.

4. A method as claimed in claim 1, wherein determining the relative two-dimensional orientation of first and second multiple-electrode leads comprises applying a stimulus to a selected group of lead electrodes and measuring the voltage at the electrodes not included in the group of electrodes to which the stimulus is applied.

5. A method as claimed in claim 1, wherein displaying the relative two-dimensional orientation of the first and second multiple-electrode leads comprises displaying the relative two-dimensional orientation of the first and second multiple-electrode leads on a programmer display.

6. A method as claimed in claim 1, further comprising:
comparing the displayed relative two-dimensional orientation of the first and second multiple-electrode leads with a display of a previously measured relative two-dimensional orientation of the first and second multiple-electrode leads.

7. A method as claimed in claim 1, further comprising:
comparing the displayed relative two-dimensional orientation of the first and second multiple-electrode leads with a display of a previously entered relative two-dimensional orientation of the first and second multiple-electrode leads.

8. An apparatus as claimed in claim 7, wherein the means for determining the relative two-dimensional orientation comprises means to determine the distances between two or more electrodes carried by the first lead and two or more electrodes carried by the second lead.

9. A method as claimed in claim 1, wherein determining the relative two-dimensional orientation comprises determining the distances between two or more electrodes carried by the first lead and two or more electrodes carried by the second lead.

10. An apparatus for use with first and second implantable leads that include respective pluralities of electrodes, the apparatus comprising:
an implantable pulse generator configured for conveying electrical stimulation energy to the first and second leads;
means for determining a relative two-dimensional orientation of the first and second leads; and
means for displaying the relative two-dimensional orientation of the first and second leads.

11. An apparatus as claimed in claim 10, further comprising:
means for comparing the displayed relative two-dimensional orientation of the first and second leads with a display of a previously measured relative two-dimensional orientation of the first and second leads.

12. An apparatus as claimed in claim 10, further comprising:
means for comparing the displayed relative two-dimensional orientation of the first and second leads with a display of a previously entered relative two-dimensional orientation of the first and second leads.

13. An apparatus for use with first and second implantable leads that include respective pluralities of electrodes, the apparatus comprising:
an implantable pulse generator configured for conveying electrical stimulation energy to the first and second leads;
a display;
circuitry to determine a relative two-dimensional orientation of the first and second leads; and
circuitry to display the relative two-dimensional orientation of the first and second leads on the display.

14. An apparatus as claimed in claim 13, wherein the display is associated with a programmer.

15. An apparatus as claimed in claim 13, wherein the circuitry to determine the relative two-dimensional orientation comprises circuitry to measure impedance vectors between lead electrodes and infer the relative two-dimensional orientation of the leads by the relative minima of the impedance vectors.

16. An apparatus as claimed in claim 13, wherein the circuitry to determine the relative two-dimensional orientation comprises circuitry to measure impedance vectors between respective electrode pairs that each include one of the electrodes on the first lead and one of the electrodes on the second lead.

17. An apparatus as claimed in claim 13, wherein the circuitry to determine the relative two-dimensional orientation comprises circuitry to apply a stimulus to a selected group of lead electrodes and measure the voltage at the electrodes not included in the group of electrodes to which the stimulus is applied.

18. An apparatus as claimed in claim 13, further comprising:
circuitry to compare the displayed relative two-dimensional orientation of the first and second leads with a display of a previously measured relative two-dimensional orientation of the first and second leads.

19. An apparatus as claimed in claim 13, further comprising:
circuitry to compare the displayed relative two-dimensional orientation of the first and second leads with a display of a previously entered relative two-dimensional orientation of the first and second leads.

20. An apparatus as claimed in claim 13, wherein the circuitry to determine the relative two-dimensional orientation comprises circuitry to determine the distances between two or more electrodes carried by the first lead and two or more electrodes carried by the second lead.

* * * * *

(12) INTER PARTES REVIEW CERTIFICATE (2366th)

United States Patent
Bradley et al.

(10) Number: US 8,682,447 K1
(45) Certificate Issued: Sep. 10, 2021

(54) APPARATUS AND METHOD FOR DETERMINING THE RELATIVE POSITION AND ORIENTATION OF NEUROSTIMULATION LEADS

(75) Inventors: Kerry Bradley; James R. Thacker (73) Assignee: BOSTON SCIENTIFIC NEUROMODULATION CORPORATION

Trial Number:

IPR2019-01341 filed Jul. 18, 2019

Inter Partes Review Certificate for:

Patent No.: 8,682,447
Issued: Mar. 25, 2014
Appl. No.: 11/343,007
Filed: Jan. 30, 2006

The results of IPR2019-01341 are reflected in this inter partes review certificate under 35 U.S.C. 318(b).

INTER PARTES REVIEW CERTIFICATE
U.S. Patent 8,682,447 K1
Trial No. IPR2019-01341
Certificate Issued Sep. 10, 2021

AS A RESULT OF THE INTER PARTES REVIEW PROCEEDING, IT HAS BEEN DETERMINED THAT:

Claim 7 is found patentable.

Claims 1-3, 5, 6 and 9 are cancelled.

\* \* \* \* \*